United States Patent [19]

Flachenecker et al.

[11] Patent Number: 5,108,391
[45] Date of Patent: Apr. 28, 1992

[54] HIGH-FREQUENCY GENERATOR FOR TISSUE CUTTING AND FOR COAGULATING IN HIGH-FREQUENCY SURGERY

[75] Inventors: Gerhard Flachenecker, Ottobrunn; Karl Fastenmeier, Munich; Heinz Lindenmeier, Planegg, all of Fed. Rep. of Germany

[73] Assignee: Karl Storz Endoscopy-America, Inc., Culver City, Calif.

[21] Appl. No.: 347,708

[22] Filed: May 5, 1989

[30] Foreign Application Priority Data

May 9, 1988 [DE] Fed. Rep. of Germany ....... 3815835

[51] Int. Cl.$^5$ .............................................. A61B 17/39
[52] U.S. Cl. ...................................... 606/38; 606/39; 606/40
[58] Field of Search .................................. 606/37–40

[56] References Cited

U.S. PATENT DOCUMENTS 4,114,623  9/1978  Meinke et al. .................... 606/38
4,617,927 10/1986  Manes ................................ 606/38

FOREIGN PATENT DOCUMENTS 0219568  4/1987  European Pat. Off. ............. 606/38
3515622 11/1986  Fed. Rep. of Germany ........ 606/38
3608833  9/1987  Fed. Rep. of Germany ........ 606/40

Primary Examiner—Lee S. Cohen
Attorney, Agent, or Firm—Donald D. Mon

[57] ABSTRACT

The invention relates to a high-frequency generator with automatic power control for tissue cutting and for coagulating in high-frequency surgery. The power control in the "cutting" mode of operation is effected with an arc control system for keeping the arc burning between the surgical probe and the tissue constant. The high-frequency generator contains a voltage-limiting circuit, which limits the output voltage to a preset maximum value if the arc control system were to adjust a higher voltage.

The advantage of the invention lies is a reduction of the mean power delivered to the patient as compared with a high-frequency generator that contains only an arc control system. The cutting quality is not adversely influenced by the power reduction.

7 Claims, 5 Drawing Sheets

HIGH-FREQUENCY GENERATOR FOR TISSUE CUTTING AND FOR COAGULATING IN HIGH-FREQUENCY SURGERY

FIELD OF THE INVENTION

The invention relates to a high-frequency generator for tissue cutting and for coagulating in high-frequency surgery.

BACKGROUND OF THE INVENTION

In high-frequency surgery, high-frequency currents are used for cutting and coagulating of human tissue. For cutting, an approximately continuous high-frequency current is supplied. In the process, a small arc is formed between the high-frequency surgical probe and the tissue to be cut. The high-frequency generator must deliver a voltage that is sufficient to strike the arc. The high-frequency current passing into the tissue heats the tissue adjacent to the high-frequency surgical probe so strongly that the cell sap volatilizes explosively and thus severs the tissue.

For coagulating, the high-frequency power is supplied in pulsed form. The mean supplied power is then low enough that explosive steam production no longer occurs. Instead, the cell sap escapes slowly and the tissue dries out without being severed. Under these conditions, however, the tissue acquires high electrical resistance. If a deep coagulation effect is to be achieved, the high frequency voltage must have relatively high pulse amplitudes, in order to maintain the current flow through the high-resistance surface.

For tissue cutting, a relatively high mean power is supplied to the patient. This conceals the known risks, such as burns, for example, for the patient. It is therfore very important to adjust the power of the high-frequency generator to the closest possible value. The output voltage must be so chosen that a sufficient tissue-severing effect just occurs, but that no excess power is delivered to the patient.

It is known that a manual generator adjustment during cutting always leads to unsatisfactory results. For this reason, a device for electrical tissue cutting in surgery is described in German Patent 2,5504,280, in which device the instantaneous condition of the cutting process is monitored by means of electrical signals. The output voltage is so adjusted with a control device that the cutting process is controlled in constant manner to a desired condition. In one embodiment, the intensity of the arc burning between the surgical probe and the tissue is measured and controlled in constant manner for this purpose. This arc control provides a significant reduction of the mean power supplied to the patient as compared with manually adjustable high-frequency generators.

BRIEF DESCRIPTION OF THE INVENTION

In the described control system, the no-load voltage of the high-frequency generator for tissue cutting can be set to any desired value that lies above the maximum voltage adjusted at any time by the control system. In practice therefore, the no-load voltage of the high-frequency generator is so chosen that it corresponds to the desired value of the pulse peaks for coagulating. In this way a very simple and inexpensive high-frequency generator can be built, in which generator the high-frequency powers for cutting and coagulating are produced with the same power generator.

From extensive measurements, however, the inventors have discovered that this feature leads to certain disadvantages in practice. In urology, for example, the tissue cuts are made in the presence of irrigating fluid. Certainly ion-low and therefore high-rsistance types of water are used preferably as irrigating fluid. After the first cuts, however, the irrigating fluid is always adulterated with some blood. Thereby the conductivity of the irrigating fluid is increased. If the high-frequency generator is inadvertently or intentionally activated, then as long as there is no contact between the surgical probe and the tissue, no arc can be formed and the control system adjusts the maximum possible high-frequency output voltage. This is approximately the no-load voltage of the high-frequency generator. Under these conditions, a current that is higher than the chosen value of the no-load voltage of the high-frequency generator flows to the patient. In reality, however, this current ought to be as small as possible in order not to stress the patient unnecessarily.

In open surgery, i.e., without the presence of irrigating fluid, the operator can activate the high-frequency generator before, for example, he touches the tissue with the surgical probe. As long as no contact with the tissue exists, no arc can strike. In this case also, the output voltage of the high-frequency generator is controlled to a high value that is practically equal to the no-load voltage. Because of the infinite control rate of the arc control system, a more intense arc than was preselected with the arc control system is initially formed during the first contact with the tissue. This initial arc is more intense the higher the no-load voltage of the high-frequency generator. It produces more intense necrosis than desired at the incision point.

The object of the invention is therefore to improve a high-frequency generator with an arc control system in such a way that the described disadvantages are avoided, i.e., the output voltage and the output power are kept as low as possible, as long as no arc burns between the surgical probe and the tissue.

The high-frequency generator according to the invention contains a measuring device that measures the output voltage of the high-frequency generator. The measured result is supplied to a voltage-limiting circuit that acts by feedback on the power generator and limits the output voltage of the high-frequency generator in the "cutting" mode of operation to a preset maximum value, in order that the output voltage cannot rise above this maximum value on the basis of the arc control system. This maximum value can be so chosen that it is not exceeded by the arc control system in all practical cases in which the surgical probe is cutting tissue. Consequently the voltage-limiting circuit is active only when the surgical probe is not in contact with the tissue. In this way the high-frequency power supplied to the patient can be effectively reduced without impairing the quality of the cutting process.

In one embodiment of the invention, the high-frequency output voltage is measured by the measuring device directly at the output of the high-frequency generator. The voltage-limiting circuit is then the most effective.

However, the output voltage of the high-frequency generator has high amplitudes, and a direct measurement is difficult to achieve under certain circumstances. In a further embodiment of the invention, it is therefore provided that the measuring device measure the output voltage in the output filter. In the output filter, there can be found points at which fractions of the output voltage are present that are either proportional or at least approximately proportional to the output voltage. These voltages are easier to process by the measuring device, and they can also be used for voltage limitation.

In many cases, power generators that operate in switching mode are used in the high-frequency generator. Such power generators have a very high efficiency and are therefore commonly used in high-frequency surgery. The power control of such generators is achieved by means of control of the operating voltage. In this case, the amplitude of the high-frequency output voltage is almost strictly proportional to the operating voltage. In one embodiment of the invention, therefore, a power generator is used that operate in switching mode, the measuring device measuring the operating voltage of the power generator and deriving therefrom the signal for voltage limitation.

Extensive measurements of the inventors have shown that the maximum high-frequency output voltages adjusted by an arc control system depend greatly on the type of application. In urology, in underwater cuts, the maximum output voltages for slow cuts on bladder tumors are approximately 250 to 300 V. For rapid, deep cuts on prostate tumors of prostate carcinomas, on the other hand, values of 350 to 450 V are attained. One embodiment of the invention therefore provides, in high-frequency generators for applications with irrigating fluids, a maximum value of the hight-frequency output voltage of 250 to 450 V.

In open surgery, without the presence of irrigating fluids, much lower maximum output voltages have been measured. The maximum high-frequency voltages adjusted by the arc control system are approximately 100 V during the application of needle electrodes and approximately 250 V during the use of high-frequency scalpels. One embodiment of the invention therefore provides, in high-frequency generators for applications without irrigating fluids, a maximum value of the high-frequency output voltage of 100 to 250 V.

For further elucidation of the invention, figures are also attached wherein:

DETAILED DESCRIPTION OF THE DRAWINGS

Figure 1:
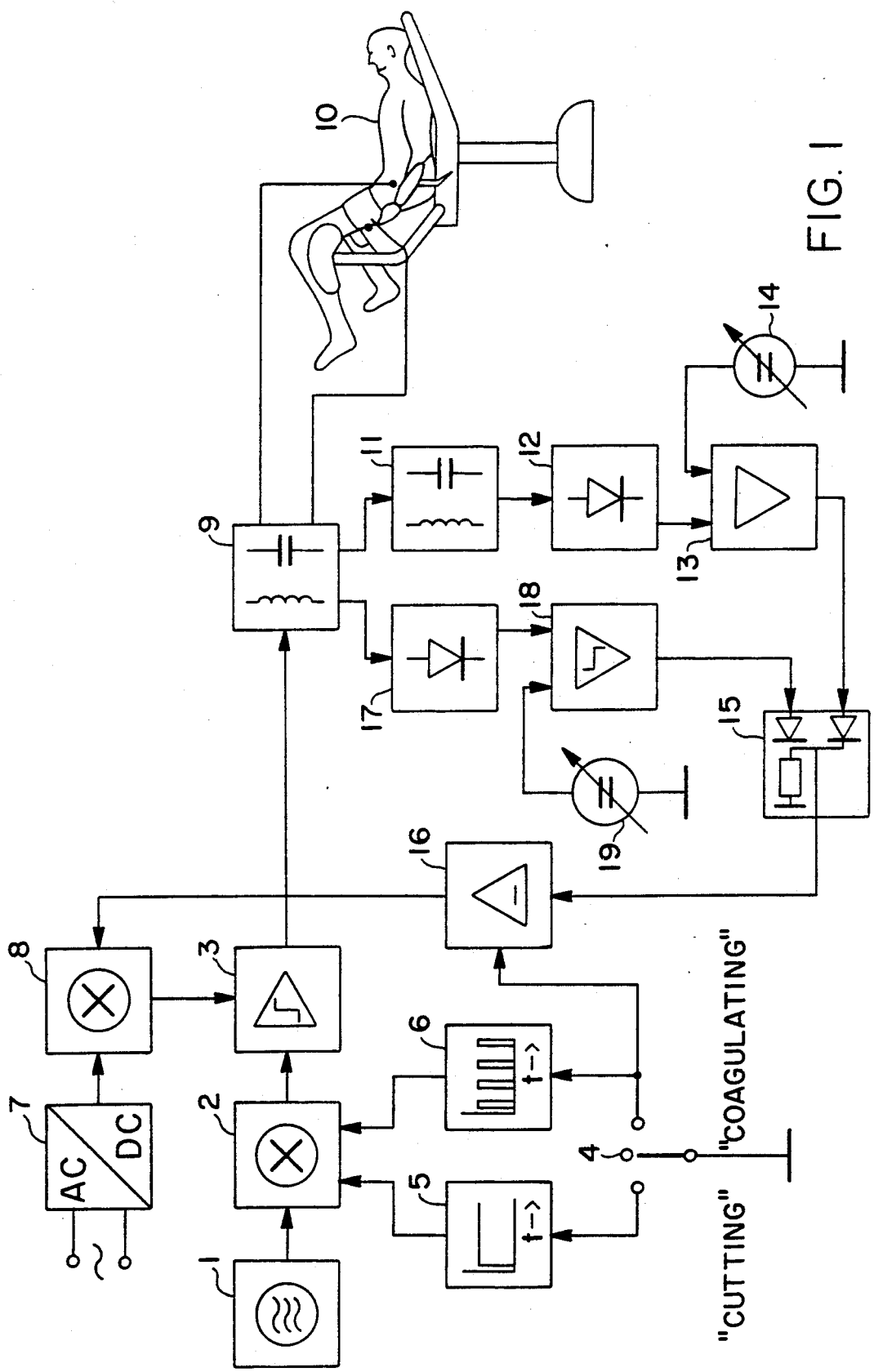
FIG. 1 shows a high-frequency generator with power generator operating in switching mode and with measurement of the output voltage in the output filter.

In FIG. 1, the block diagram of a high-frequency generator according to the invention with power generator operating in switching mode and with measurement of the ouput voltage in the output filter is shown as an example. The oscillator 1, via the modulator 2, controls the power amplifier 3. The time response of the high-frequency generator can be controlled with the modulator 2. For this purpose, the modulator 2 is driven, via the switching elements 5 and 6, by the switch 4, which can be activated in the "cutting" or "coagulating" positions. These timing elements activate the modulator either continuously, as in cutting or in pulsed mode, as in coagulating.

This type of modulation is only one simple example out of many possibilities. For example, high-frequency generators are known in which the switching element 5 also performs a time limitation of the activation state. For switching element 6 in particular, even more complicated approaches with additional functions, such as, for example, arc-dependent switch-over between continuous power and pulsed power, have been disclosed. However, the simple switching elements 5 and 6 of FIG. 1 are sufficient to explain the invention. The power generator 3 operates in switching mode. It is supplied with operating voltage in the power rectifier 7 and the d.c. voltage regulator. 8. The high-frequency output voltage of the power generator can be adjusted with the d.c. voltage regulator 8. This output voltage is relayed via the output filter 9 in known manner to the surgical probe, i.e., to the patient 10.

A signal relating to the condition of the cutting process is derived from the output filter, in the present example, the filter 11 is used for this purpose. It is matched to one or more harmonics of the generator frequency. Their frequencies are produced by the nonlinear response of the arc burning at the surgical probe. Their amplitudes are a direct measure of the intensity of the arc, and they can be used for control of the arc intensity. For this purpose the harmonics filtered out in the filter 11 are rectified in the rectifier 12 and are compared in the differential amplifier 13 with an adjustable setpoint value from the setpoint device 14. The result of this comparison is passed via the summing element 15 and the control amplifier 16 to the d.c. voltage regulator 8. In this way the control loop is closed and the arc intensity is controlled automatically to the value specified by the setpoint device 14.

Since this control function is intended to be effective only in the cutting mode of operation, the control amplifier 16 is deactivated in the "coagulating" position of the switch 4. In order to ensure the correct phase for the control loop, the control amplifier 16 is designed as an inverting amplifier.

From the output filter 9, a voltage proportional to the output voltage of the high-frequency generator is now further tapped and supplied to the rectifier 17. The output signal thereof is compared in the comparator 18 with a set point value delivered by a setpoint device 19. If the signal delivered by the rectifier 17 exceeds the value delivered by the setpoint device 19, the output signal of the comparator 18 intervenes via the summing element 15 in the control process and prevents an increase of the high-frequency output voltage above the value specified by the setpoint device 19. In this way, the high-frequency output voltage is limited to the preset value.

The value of the setpoint device 19 must naturally allow for the conversion factors of the output filter 9 and of the rectifier 17.

It must be mentioned that, for reasons of clarity, a very simple are control system and a very simple voltage-limitation circuit are shown in this example. In practice, much more extensive circuits based on principles of automatic control engineering which are known in themselves can be constructed in order to achieve better control and limitation properties.

Figure 2:
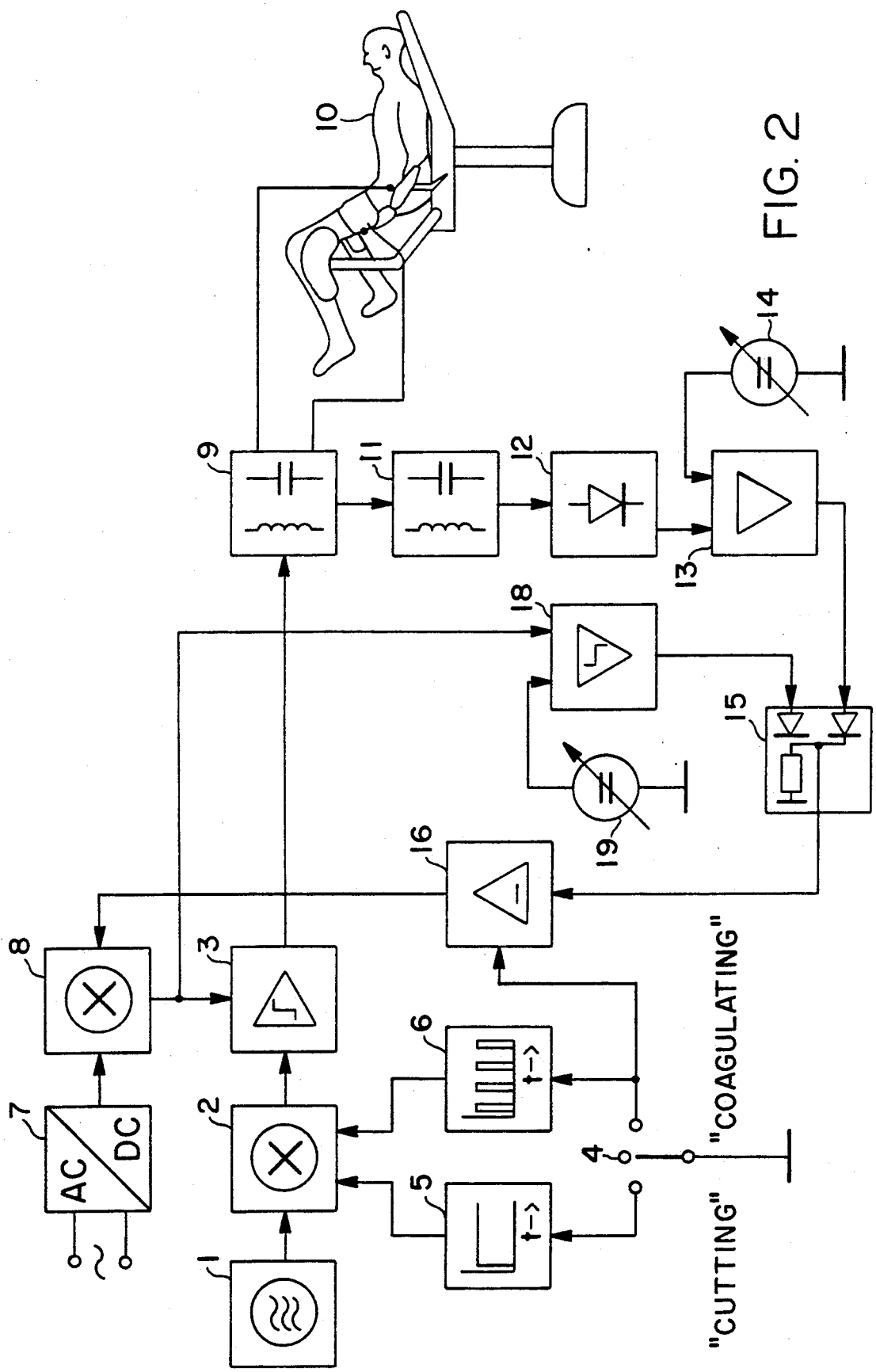
FIG. 2 shows a high-frequency generator with power generator operating in switching mode and with measurement of the operating voltage of the power generator.

FIG. 2 shows the block diagram of a circuit similar to that of FIG. 1. Since in these examples a power generator with switching operation is used, the operating voltage of the power generator can be used a a measure of its high-frequency output voltage. The output voltage of the d.c. voltage regulator 8 is therefore supplied to the comparator 18 as a signal and compared with the value of the setpoint device 19. Naturally, the conversion factor between the operating voltage of the power generators 3 and its high-frequency output voltage must be allowed for in this case also in the value of the setpoint device 18.

Figure 3:
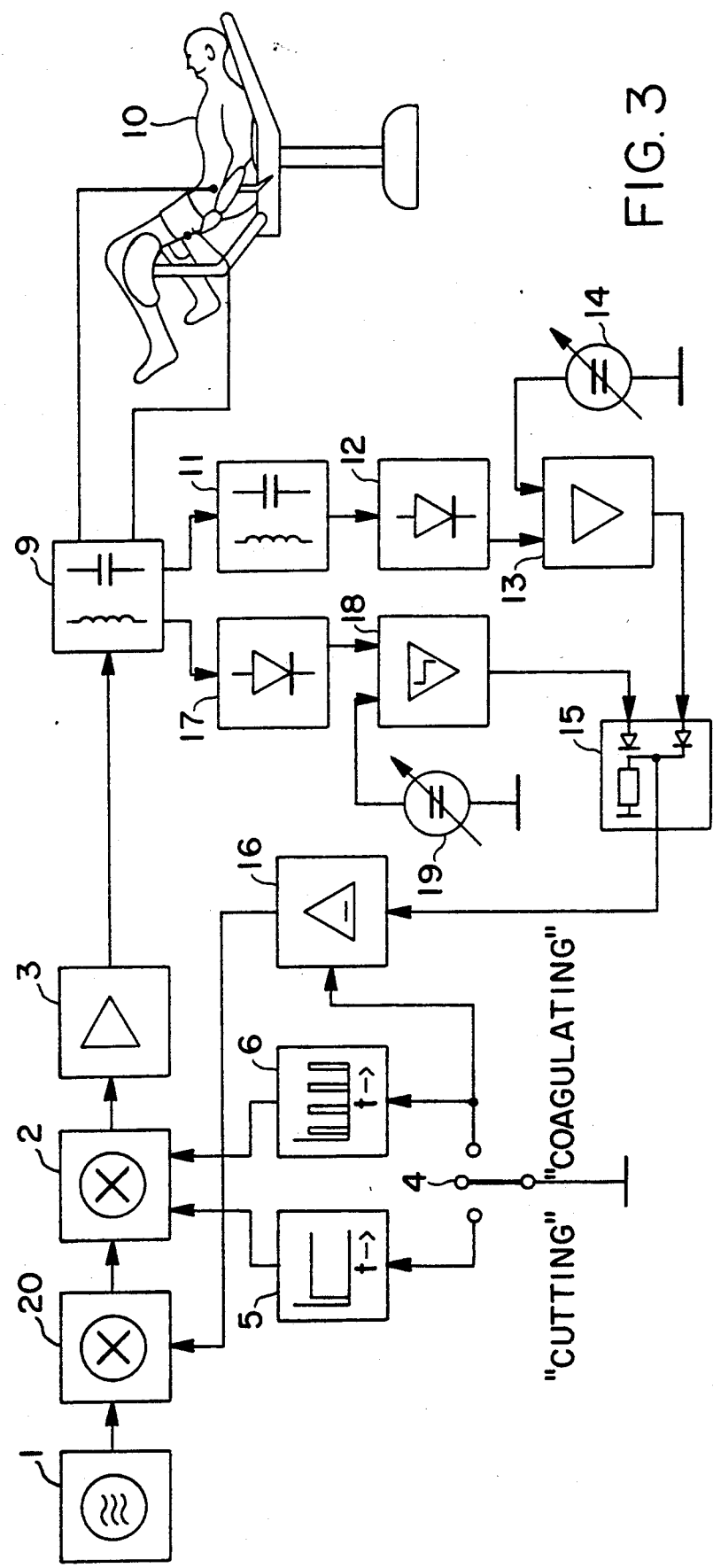
FIG. 3 shows a high-frequency generator with linearly operating power generator and with measurement of the output voltage in the output filter.

The block diagram of a high-frequency with linear power generator is illustrated in FIG. 3. Since no control of the high-frequency output voltage can be effected here via the operating voltage of the power generator, the operating-voltage supply is not even shown in this example. In this case a further modulator 20 is provided for the purpose, which modulator is controlled by the output signal of the control amplifier 16 and which performs corresponding arc control and voltage limitation.

Figure 4:
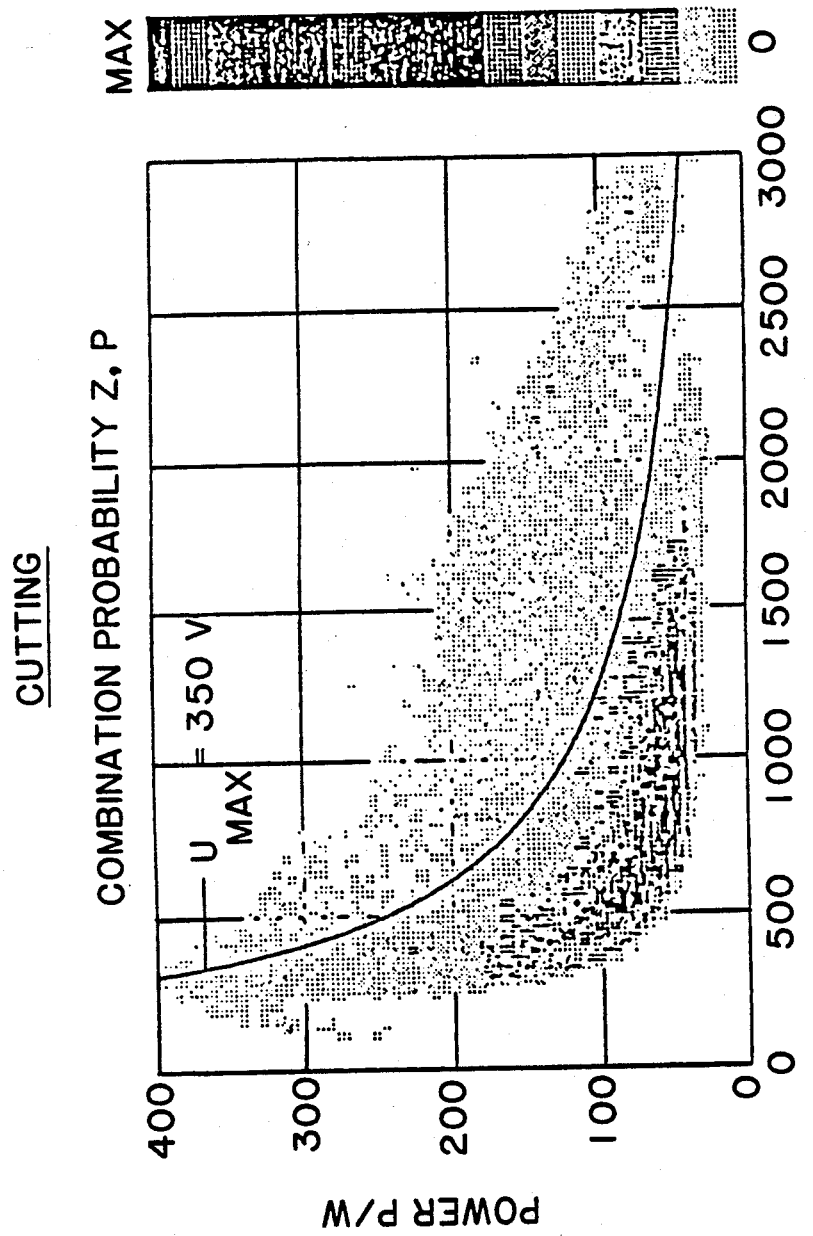
FIG. 4 shows the combination probability for impedance and power for a prostrate resection with a high-frequency generator without voltage limitation.
Figure 5:
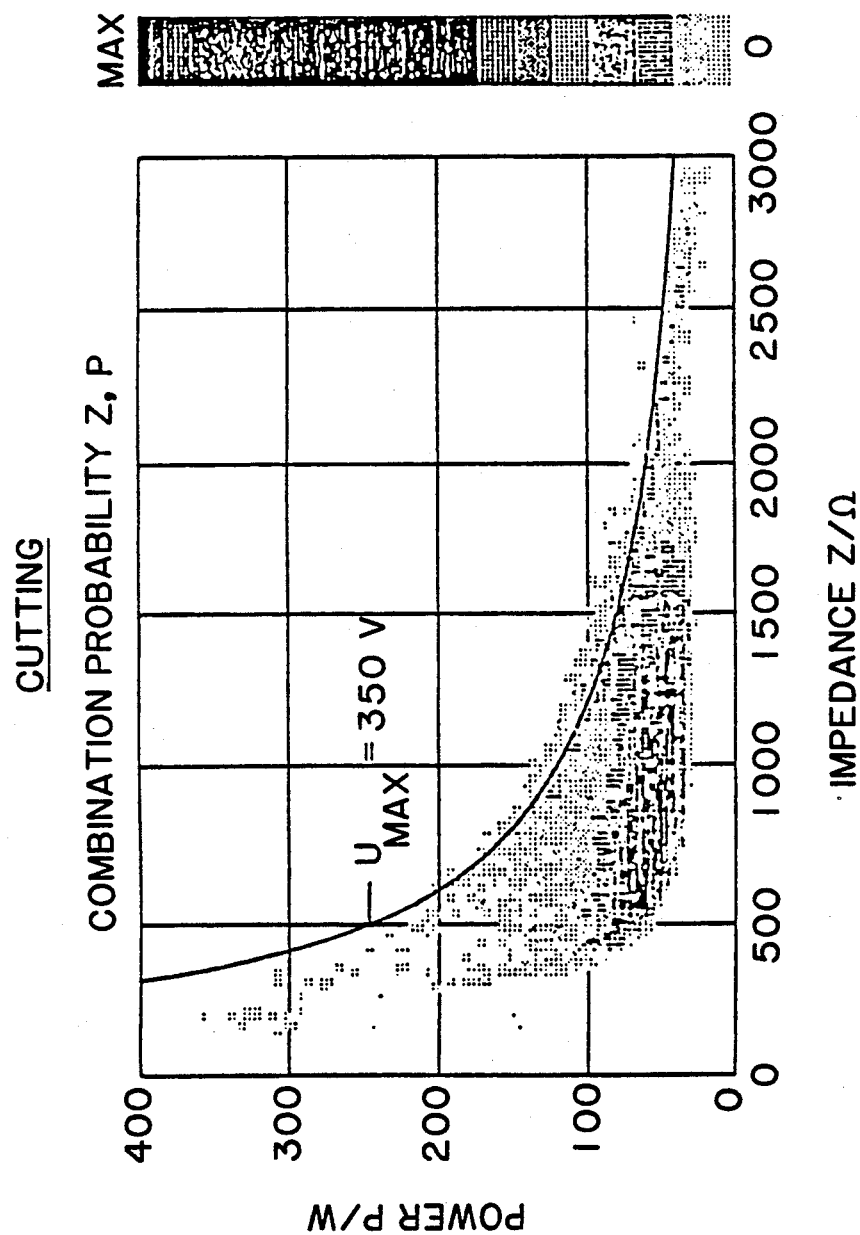
FIG. 5 shows the combination probability for impedance and power for a prostate resection with a high-frequency generator with voltage limitation.

FIGS. 4 and 5 show advances which can be achieved with a high-frequency generator according to the invention. The result of a prostate resection recorded completely by instrumental means is plotted in FIG. 4. The chosen form of representation was the combination probability for impedance and power during cutting. Approximately 50 g of tumor tissue was removed during the operation. The measurement was performed with a sampling frequency of approximately 50 measurements per second. In the process, approximately 30,000 sets of the three measured values for voltage, current and phase shift were recorded, from which the values for power and impedance were computed subsequently. In FIG. 4, the measured-value combinations of impedance and power are plotted as a function of their frequency, i.e., their probability in different degrees of blackness. An appropriate gray scale is given for calibration along the right margin.

A distinct accumulation is to be seen at the bottom left of the combination probability in FIG. 4. Detailed analysis of the measured results have shown that this corresponds to the normal cutting processes with operating arc control. The rising branch at approximately 400 ohm and 200 to 400 W represents the increased power requirement for incision, the arc control system operating normally even here.

A curve labelled $U_{max}=350$ v is also plotted in FIG. 4. It represents the geometric locus of all measured values for which the instantaneous high-frequency output voltage of the high-frequency generator was precisely 350 v. The further reaching analyses of the measured results performed by the inventors have shown that the curve for this operation lies approximately at the boundary between normal cutting processes and the power delivery to the irrigating fluid. All measured values that lie above this curve increase the power delivery to the patient as described above, without being relevant for the cutting process. If the output voltage of the high-frequency generator had been limited to 350 V in this operation, all values measured on the other side of the plotted curve could have been greatly reduced in their power, despite which the operator would not have observed a loss of cutting quality.

Finally, in FIG. 5, the measured values of a prostate resection comparable to FIG. 4 are plotted, in which resection, however, the high-frequency generator was configured according to the invention. The combination probability for impedance and power shows, because of the limitation of the maximum output voltage to 350 V, a distinct decrease of the mean power.

This invention is not to be limited by the embodiments shown by the drawings and described in the description, which are given by way of example and not of limitation, but only in accordance with the scope of the appended claims.

I claim:

1. In a high frequency generator for high-frequency surgery in which electrical power is supplied to a surgical probe, which high-frequency generator can selectively generate electrical power for a tissue cutting mode, and for a coagulation mode, said high-frequency generator including a power generator means which can be switched in the tissue cutting mode to continuous power delivery, and an arc control system which during tissue cutting controls the intensity of an arc which burns between the surgical probe and tissue being cut to maintain the arc at a preselected value, the improvement comprising:
    a measuring device means measuring the high-frequency output voltage of said high frequency generator or a variable which is proportional thereto:
    measuring signal means responsive to said measuring device means forming a measuring signal; and
    voltage-limiting circuitry means receiving and responsive to said measuring signal, said voltage-limiting circuitry means being so constructed as adjustably to sense and to limit the output voltage of the high-frequency generator, limiting it to a preset maximum value when the probe is not in contact with tissue, and the high-frequency output voltage under control of the arc control system would otherwise rise to values higher than said preset maximum value, said voltage-limiting circuitry means being effective when the tissue cutting mode is selected.

2. A high-frequency generator according to claim 1, characterized in that the measuring device means (17) measures the high-frequency output voltage at the output of the high-frequency generator.

3. A high-frequency generator according to claim 1, characterized in that said high frequency generator's output is received by a high-frequency output filter, and said measuring device means measures the output of said filter.

4. A high frequency generator according to claim 1, characterized in that said power generator means itself operates in a switching mode to generate its own output, and its own said output is supplied to a power amplifier means, and in that said measuring device means responds to the operating voltage of said power amplifier means.

5. A high-frequency generator according to claim 1 for applications in the presence of irrigating fluids, characterized in that the preset maximum value of the high-frequency output voltage lies between 250 and 450 volts.

6. A high-frequency generator according to claim 1 for applications without the presence of irrigating fluids, characterized in that the preset maximum value of the high-frequency output voltage lies between 100 and 300 volts.

7. An improvement in a method to protect a surgical patient from excessive current loads applied to said patient during electrosurgery when an electrosurgical appliance having a probe intended to contact tissue is applied to his tissues, said appliance being operable selectively in either a coagulation mode or in a tissue cutting mode under the control of a circuit which is responsive to circumstances accompanying the existence or absence of an arc between the probe and tissue in a tissue-cutting mode, and said method contemplating circumstances where, when the probe is in contact with tissue it may be immersed in conductive fluids between the probe and the tissue, said improvement being characterized by limiting the maximum output voltage of a frequency-generating generator with a voltage limiting circuit whose preset selective voltage limitation is above the maximum anticipated voltage expected to be required for the cutting mode when the probe contacts the tissue, whereby the patient is protected from excessive currents and voltage in the tissue-cutting mode when the probe does not contact the tissue, said method being effective only when the appliance is in the tissue cutting mode.

* * * * *